United States Patent [19]

Skotnicki et al.

[11] Patent Number: 5,281,608

[45] Date of Patent: Jan. 25, 1994

[54] SUBSTITUTED TETRAHYDROPYRIDO[3',4':4,5]-PYRROLO[3,2-C]QUINOLINES

[75] Inventors: Jerauld S. Skotnicki, Allentown; Robert M. Kearney, Lawrenceville, both of N.J.

[73] Assignee: American Home Products Corporation, New York, N.Y.

[21] Appl. No.: 936,827

[22] Filed: Aug. 28, 1992

[51] Int. Cl.⁵ .................. C07D 295/10; A61K 31/47
[52] U.S. Cl. .......................... 514/287; 514/886; 546/64
[58] Field of Search .................. 546/64; 514/287, 886

[56] References Cited

U.S. PATENT DOCUMENTS

| | | | |
|---|---|---|---|
| 3,917,599 | 11/1975 | Saxena et al. | 546/64 |
| 4,266,060 | 5/1981 | Bisagni et al. | 546/64 |
| 4,771,052 | 9/1988 | Schönafinger et al. | 514/287 |

OTHER PUBLICATIONS

Helissey et al., "Heterocyclic quinones . . . ", Fac. Sci Pharm. Biol., Univ. Rene Descartes, Chem. Pharm. Bull. 37(9) 2413-16 1989.
Schonafinger, et al., "Synthesis . . . ", J. Heterocyclic Chem. 25 (2), 535-7, 1988.

*Primary Examiner*—Marianne M. Cintins
*Assistant Examiner*—Catherine S. Scalzo Kilby
*Attorney, Agent, or Firm*—George Tarnowski

[57] ABSTRACT

There are disclosed compounds of the formula

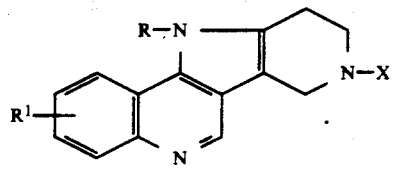

wherein
R is hydrogen, lower alkyl or phenyl;
$R^1$ is hydrogen, lower alkyl, phenyl, halo, hydroxy, lower alkoxy or trifluoromethyl;
$R^2$ is phenyl, phenylloweralkyl, thienyl, furyl, pyrrolyl, pyridyl, benzothienyl, benzofuryl, indolyl, quinolinyl, or any of the foregoing substituted with halo, lower alkyl, lower alkylcarbonyl, benzoyl, carboxy, lower alkoxycarbonyl, $OR^3$, $N(R^3)_2$, $CON(R^3)_2$, phenylsulfonyl, lower alkylsulfonyl, cyano, nitro or trifluoromethyl;
$R^3$ is hydrogen, lower alkyl or phenyl;

X is $R^2$, $-CO_2R^2$, $-CO_2R^4$, $-\underset{\underset{Y}{\parallel}}{C}NHR^2$, $-\underset{\underset{Y}{\parallel}}{C}NHR^4$, $-SO_2R^2$, $-SO_2R^4$, $-\underset{\underset{}{\overset{Y}{\parallel}}}{C}NHSO_2R^2$ or $-\underset{\underset{}{\overset{Y}{\parallel}}}{C}NHSO_2R^4$;

$R^4$ is lower alkyl;
Y is —O— or —S—;

which, by virtue of their ability to inhibit interleukin 1, and to modify the balance between bone production and bone resorption, are of use as anti-inflammatory agents, in the treatment of disease states involving enzymatic tissue destruction, and in the treatment of osteoporosis, and are also intermediates in the preparation of other compounds which possess the ability to inhibit interleukin 1.

23 Claims, No Drawings

SUBSTITUTED TETRAHYDROPYRIDO[3',4':4,5]-PYRROLO[3,2-C]QUINOLINES

This invention relates to novel compounds possessing interleukin 1 (IL-1) antagonist activity and having anti-inflammatory activity and having utility in modifying the balance between bone production and bone resorption in mammals.

Interleukin 1 (IL-1) is a peptide hormone exhibiting a number of immune and inflammatory actions [Dinarello, *Rev. Inf. Dis.* 6, 51 (1984)]. IL-1 is produced, in response to inflammatory stimuli, by leukocytes such as macrophages and polymorphonuclear cells, as well as by a variety of other cell types such as synovial cells, endothelial cells and keratinocytes, and it mediates several biological responses of leukocytes on other tissue targets such as bone, articular joints, liver, hypothalamus, and brain.

IL-1 was originally shown to augment the proliferation of T-lymphocytes for which it was named lymphocyte activating factor (LAF), and is believed to be important for the generation of T cell-dependent immune responses.

There is evidence to suggest a relationship between IL-1 and pathology in various diseases, particularly immunoinflammatory disorders such as rheumatoid arthritis [Dinarello et al., *Ann. Rev. Med.* 37, 173 (1986)]. IL-1 induces acute inflammatory responses producing soft tissue swelling (edema and erythema) [Granstein et al., *J. Clin. Invest.*, 77, 1010 (1986)]. It is a chemoattractant for polymorphonuclear leukocytes (PMN) and induces the activation and migration of these cells into tissues. IL-1 also stimulates the production of prostaglandin $E_2$, a potent inflammatory arachidonic acid metabolite, by a variety of cells and tissues including chondrocytes and synovial cells [Mizel et al., *Proc. Nat'l. Acad. Sci.*, 78, 2474 (1981) and Chang et al., *J. Immunol.*, 136, 1283 (1986)] and hypothalamic tissue. This effect on the hypothalamus is thought to be responsible for fever production. IL-1 can induce articular joint destruction by stimulating the production of a variety of hydrolytic enzymes (neutral proteases such as collagenase, glycosaminoglycanases, etc.) which degrade cartilage matrix proteins (collagen, proteoglycan, etc.) by synovial cells, chondrocytes, and fibroblasts [Dayer et al., *Science*, 195, 181 (1977) and Postlethwaite et al., *J. Exp. Med.*, 157, 801 (1983)]. Furthermore, IL-1 induces hyperproliferation of dermal and synovial fibroblasts and is a potent inducer of bone resorption [Wood et al., *J. Immunol.*, 134, 895 (1985) and Gilman and Kimball, *Agents and Actions*, 16, 468 (1985)]. is a potent inducer of bone resorption [Wood et al., *J. Immunol.*, 134, 895 (1985) and Gilman and Kimball, *Agents and Actions*, 16, 468 (1985)].

Finally, IL-1 mediates acute phase reactions including alterations in plasma divalent cations, increased synthesis by liver cells of acute phase proteins (C-reactive protein, serum amyloid A, etc.) and fever. Accordingly, compounds which have IL-1 antagonist activity and thereby inhibit the biological effects of IL-1 can be advantageously used to block pathologies in which one or more of these events occur such as rheumatoid arthritis, osteoarthritis and related disorders [Rodnan and Schumacher, eds, "Primer on the Arthritic Diseases" 8 ed. Atlanta, 1983], psoriasis and other inflammatory/proliferative skin disorders as well as diseases in which the secretion of collagenase (and other tissue hydrolyzing neutral proteinases) has been implicated as a causative factor, including periodontal disease, tumor invasiveness, and epidermolysis bullosa [Perez-Tamayo, *Amer. J. Pathol.*, 92, 509 (1978) and Harris and Krane, *N. Engl. J. Med.*, 291, 652 (1974)] and so forth.

Osteoporosis is a skeletal disorder which is evidenced by a decrease in bone density throughout the body. In fact, both the bone mineral (calcium phosphate called "hydroxyapatite") and the bone matrix (major protein called "collagen") are slowly lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal, that is, new bone is continuously being formed and old bone is continuously being resorbed. However, in animals suffering from an osteoporotic condition, net bone resorption exceeds bone formation.

The mechanism of bone loss is at present poorly understood. Moreover, the present methods of treatment are generally unsatisfactory. These include anabolic agents, various drugs containing phosphorous, Vitamin D, calcium salts, fluorides and calcitonin. Estrogen replacement therapy has been the therapy of choice for osteoporosis in post-menopausal women. Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis. Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After previous bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include phosphonates, calcitonin and mithramycin. However, all of these drugs suffer serious drawbacks.

It has now been found that certain novel substituted pyrido[3',4':4,5]-pyrrolo[3,2-c]quinolines antagonize the activity of IL-1, and so are useful as antiinflammatory agents and also in modifying the balance between bone production and bone resorption in mammals. The present invention provides novel compounds having the formula:

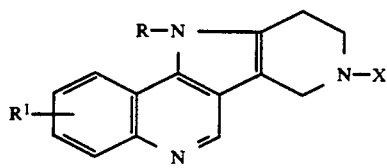

wherein
R is hydrogen, lower alkyl or phenyl;
$R^1$ is hydrogen, lower alkyl, phenyl, halo, hydroxy, lower alkoxy or trifluoromethyl;
$R^2$ is phenyl, phenylloweralkyl, thienyl, furyl, pyrrolyl, pyridyl, benzothienyl, benzofuryl, indolyl, quinolinyl, or any of the foregoing substituted with halo, lower alkyl, lower alkylcarbonyl, benzoyl, carboxy, lower alkoxycarbonyl, $OR^3$, $N(R^3)_2$, $CON(R^3)_2$, phenylsulfonyl, lower alkylsulfonyl, cyano, nitro or trifluoromethyl;
$R^3$ is hydrogen, lower alkyl or phenyl;

X is $R^2$, $-CO_2R^2$, $-CO_2R^4$, $-\underset{\underset{Y}{\|}}{C}NHR^2$, $-\underset{\underset{Y}{\|}}{C}NHR^4$, $-SO_2R^2$, $-SO_2R^4$, $-\underset{\underset{Y}{\|}}{C}NHSO_2R^2$ or $-\underset{\underset{Y}{\|}}{C}NHSO_2R^4$;

$R^4$ is lower alkyl;
Y is $-O-$ or $-S-$.

Also, there is disclosed a method for the treatment of inflammatory conditions and of osteoporosis which comprises the administration of a therapeutically effective amount of a compound having the formula

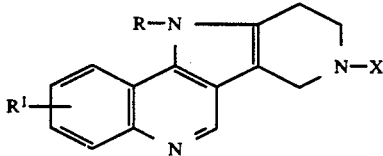

wherein
R is hydrogen, lower alkyl or phenyl;
$R^1$ is hydrogen, lower alkyl, phenyl, halo, hydroxy, lower alkoxy or trifluoromethyl;
$R^2$ is phenyl, benzoyl, phenylloweralkyl, phenylsulfonyl, thienyl, furyl, pyrrolyl, pyridyl, benzothienyl, benzofuryl, indolyl, quinolinyl, or any of the foregoing substituted with halo, lower alkyl, lower alkylcarbonyl, benzoyl, carboxy, lower alkoxycarbonyl, $OR^3$, $N(R^3)_2$, $CON(R^3)_2$, phenylsulfonyl, lower alkylsulfonyl, cyano or trifluoromethyl;
$R^3$ is hydrogen, lower alkyl or phenyl;

X is $-\underset{\underset{Y}{\|}}{C}R^2$ and $-\underset{\underset{Y}{\|}}{C}R^3$; and Y is $-O-$ or $-S-$.

The terms "lower alkyl" and "lower alkoxy" refer to moieties having 1 to 6 carbon atoms in the carbon chain. The term "halo" refers to fluoro, chloro and bromo.

The compounds of the invention, in addition to possessing the above-indicated activities are also intermediates for producing compounds embraced by the following formula and also possessing the ability to inhibit interleukin 1:

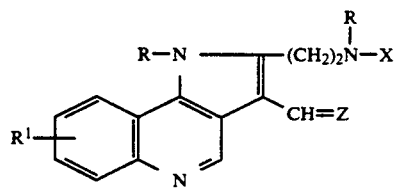

wherein
X is $R^2$, $-\underset{\underset{}{\overset{O}{\|}}}{C}R^2$ or $-SO_2R^2$;
R is hydrogen, lower alkyl or phenyl;
$R^1$ is hydrogen, lower alkyl, phenyl, halo, lower alkoxy, hydroxy or trifluoromethyl;
$R^2$ is phenyl, thienyl, furyl, pyridyl, benzothienyl, benzofuryl, indolyl, quinolinyl, substituted with halo, lower alkylcarbonyl, benzoyl, carboxy, lower alkoxycarbonyl, $CON(R)_2$, $SO_3R^3$, cyano or trifluoromethyl;
$R^3$ is lower alkyl or phenyl;
Z is $-O-$, $-NNHR^4$, $-NOR^4$, $-NNH\underset{\underset{}{\overset{Y}{\|}}}{C}R^4$;

Y is $-O-$ or $-S-$; and
$R^4$ is hydrogen, lower alkyl, phenyl, thienyl, furyl, or pyridyl or any of the foregoing substituted with halo, lower alkyl, carboxyl, lower alkoxycarbonyl, cyano, $CON(R)_2$, $SO_3R_3$, trifluoromethyl, lower alkoxy or hydroxy.

The compounds of the invention can be prepared according to the following reaction scheme, in which the various tetrahydropyrido ring N-substituents are introduced onto a suitable starting 8,9,10,11-tetrahydro-7H-pyrido[3',4':4,5]-pyrrolo[3,2-c]quinoline, which in turn, can be prepared according to the method disclosed in *Journal of Heterocyclic Chemistry*, 25, 535 (1988):

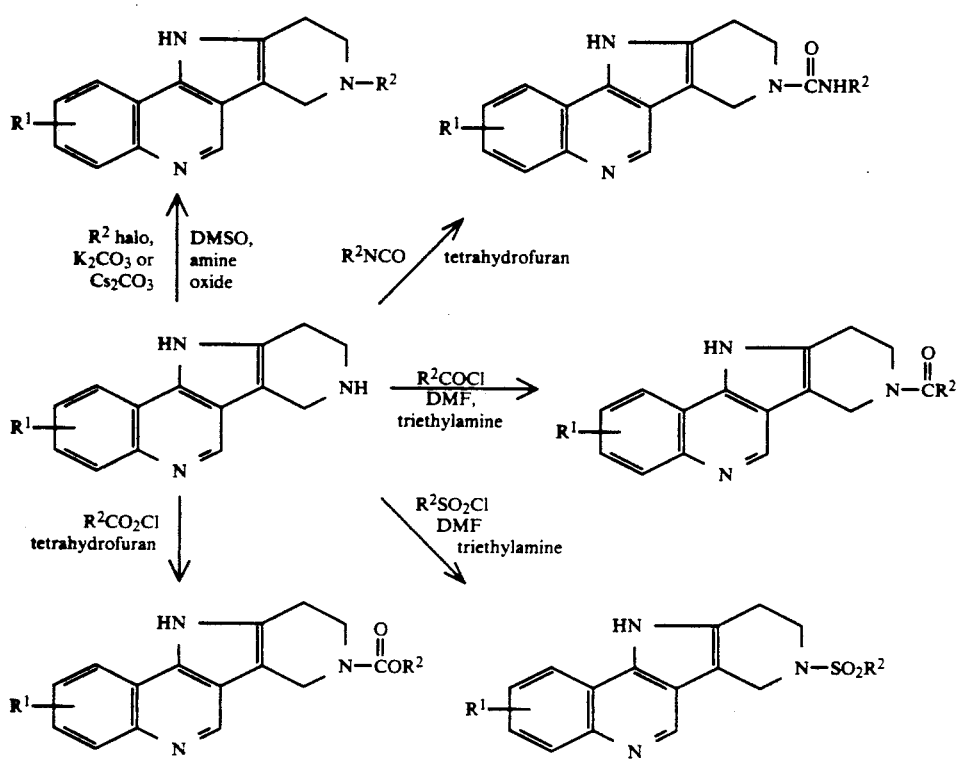

The compounds of the invention can also be prepared by the following method:

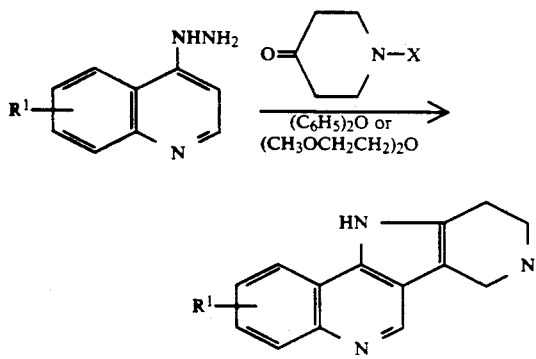

In addition to the heterocyclic amine already discussed, all starting materials used in the above outlined preparative sequences are available commercially or can be prepared by conventional methods disclosed in the chemical literature.

The compounds of the invention, by virtue of the ability to antagonize interleukin 1, are useful in the treatment of such diseases as rheumatoid arthritis, osteoarthritis, tendinitis, bursitis and similar conditions involving inflammation, as well as psoriasis and other inflammatory/proliferative skin disorders. Moreover, the compounds are useful in treating disease states involving enzymatic tissue destruction, for example, conditions in which collagenase has been implicated as a causative factor, such as rheumatoid arthritis joint destruction, periodontal disease, tumor invasiveness, corneal ulcerations, epidermolysis bullosa and the like. Additionally, since compounds the invention are able to modify the balance between bone production and bone resorption, they are useful in the treatment of osteoporosis.

When the compounds of the invention are employed as anti-inflammatory agents or in the treatment of osteoporosis, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For topical administration, the compounds may be formulated in the form of dusting powders, solutions, creams, lotions or aerosols in pharmaceutically acceptable vehicles, which are applied to affected portions of the skin.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as single unit dose, or if desired, the dosage may be divided into convenient subunits administered at suitable times throughout the day.

The interleukin 1 antagonist activity, as well as the antiinflammatory effects of the compounds of the invention and their ability to modify the balance between bone production and bone resorption may be demonstrated by standard pharmacological procedures, which are described more fully in the examples given hereinafter.

These procedures illustrate the ability of the compounds of the invention to inhibit the IL-1-induced release of neutral protease from articular chondrocytes and to inhibit basal or stimulated bone resorption in culture.

The following examples show the preparation and pharmacological testing of compounds within the invention.

EXAMPLE 1

3-Chloro-8,9,10,11-tetrahydro-8-[4-(methylsulfonyl)-phenyl]-7H-pyrido[3',4':4,5]pyrrolo[3,2-c]quinoline A mixture of 1.5 g (5.8 mmol) of 3-chloro-8,9,10,11-tetrahydro-7H-pyrido[3',4':4,5]pyrrolo[3,2-c]quinoline prepared according to the method reported in *J. Heterocyclic Chemistry*, 25, 535 (1988), 1.01 g (5.8 mmol) of p-fluoromethylsulfone, 0.68 g (5.8 mmol) of 4-methylmorpholine N-oxide, 3.78 g (11.6 mmol) of $Cs_2CO_3$ and 10 ml of dimethylsulfoxide is stirred overnight at 80° C. The reaction mixture is allowed to cool and is diluted with water to yield a brown precipitate which is collected by filtration and dried. The crude product is purified by flash column chromatography (6% methanol in chloroform) to yield 0.15 g (6%) of the title compound as a tan solid: m.p.>250° C.; IR (KBr) 3280, 1580, 1145 cm$^{-1}$; NMR (DMSO-d$_6$) δ12.4 (s, 1H), 9.1 (s, 1H), 8.3 (d, 1H), 8.0 (d, 1H), 7.7 (d, 2H), 7.6 (s, 1H), 7.2 (d, 1H), 4.8 (s, 2H), 3.9 (t, 2H), 3.1–3.0 (m, 5H); m/e 411.

Analysis for: $C_{21}H_{18}ClN_3O_2S \cdot \frac{3}{4} H_2O$; Calculated: C, 59.29; H, 4.62; N, 9.88. Found: C, 59.11; H, 4.50; N, 9.69.

EXAMPLE 2

4-(3-Chloro-8,9,10,11-tetrahydro-7H-pyrido[3',4':4,5]-pyrrolo[3,2-c]quinolin-8-yl)benzoic acid ethyl ester A mixture of 1.5 g (5.8 mmol) of 3-chloro-8,9,10,11-tetrahydro-7H-pyrido[3',4':4,5]pyrrolo[3,2-c]quinoline, 0.979 g (5.8 mmol) of ethyl 4-fluorobenzoate, 0.68 g (5.8 mmol) of 4-methylmorpholine N-oxide, 3.78 g (11.6 mmol) of $Cs_2CO_3$ and 10 ml of dimethylsulfoxide is stirred overnight at 80° C. The reaction mixture is allowed to cool and is diluted with water to yield a brown precipitate which is collected by filtration and dried. The crude product is purified by flash column chromatography (5% methanol in chloroform) to yield 0.055 g (2%) of the title compound as a yellow solid: m.p. 241°–243° C.; m/e 405.

Analysis for: $C_{23}H_{20}ClN_3O_2$. Calculated: C, 68.06; H, 4.97; N, 10.35. Found: C, 67.85; H, 5.01; N, 10.47.

EXAMPLE 3

4-(3-Chloro-8,9,10,11-tetrahydro-7H-pyrido[3',4':4,5]-pyrrolo[3,2-c]quinolin-8-yl)benzonitrile A solution of 1.00 g (3.88 mmol) of 3-chloro-8,9,10,11-tetrahydro-7H-pyrido[3',4':4,5]pyrrolo[3,2-c]quinoline, 0.47 g (3.88 mmol) of p-fluorobenzonitrile, 0.54 g (3.88 mmol) of $K_2CO_3$ and 8 ml of dimethylsulfoxide are stirred at 80° C. for 3 days. The reaction mixture is allowed to cool and is diluted with water producing a brown precipitate which is collected by filtration and dried. The crude product is purified by flash column chromatography (5% methanol in chloroform) to yield 0.06 g (4%) of the title compound as a pink solid: m.p.>275° C.; m/e 358.

Analysis for: $C_{21}H_{15}ClN_4 \cdot \frac{1}{2} H_2O$. Calculated: C, 68.57; H, 4.39; N, 15.23. Found: C, 68.73; H, 4.17; N, 14.90.

EXAMPLE 4

3-Chloro-8,9,10,11-tetrahydro-8-(2-thienylcarbonyl)-7H-pyrido[3',4':4,5]pyrrolo[3,2-c]quinoline To a mixture of 0.40 g (1.55 mmol) of 3-chloro-8,9,10,11-tetrahydro-7H-pyrido[3',4':4,5]pyrrolo[3,2-c]quinoline and 2 ml of dimethylformamide at 0° C. is added 0.23 g (1.55 mmol) of 2-thiophencarbonylchloride. The reaction mixture solution is allowed to stir overnight while slowly reaching room temperature. The reaction mixture is then diluted with water producing a tan precipitate which is collected by filtration, washed with water and dried to yield 0.282 (50%) of the title compound as a tan solid: m.p.>250° C.; IR (KBr) 3420, 1640, 1440 cm$^{-1}$; NMR (DMSO-d$_6$) δ14.1 (s, 1H), 9.6 (s, 1H), 8.6 (d, 1H), 8.3 (s, 1H), 8.0 (d, 1H), 7.8 (d, 1H), 7.6 (s, 1H), 7.2 (d, 1H), 5.0 (s, 2H), 4.0 (t, 2H), 3.1 (m, 2H); m/e 368 (M+H).

Analysis for: $C_{19}H_{14}ClN_3OS$. Calculated: C, 62.04; H, 3.84; N, 11.42. Found: C, 61.75; H, 3.92; N, 11.48.

EXAMPLE 5

3-Chloro-8-(4-cyanobenzoyl)-8,9,10,11-tetrahydro-7H-pyrido[3',4':4,5]pyrrolo[3,2-c]quinoline To a mixture of 0.40 g (1.55 mmol) of 3-chloro-8,9,10,11-tetrahydro-7H-pyrido[3',4':4,5]pyrrolo[3,2-c]quinoline, 0.188 g (1.86 mmol) of triethylamine and 15 ml of tetrahydrofuran at 0° C. is added 0.275 g (1.55 mmol) of 4-cyanobenzoyl chloride dropwise and the reaction mixture is allowed to stir overnight while slowly reaching room temperature. A precipitate is formed overnight which is collected by filtration, washed with water and ether and dried to yield a crude product which is triturated with methanol/chloroform to yield 0.14 g (23%) of the title compound as a white solid: m.p.>300° C.; m/e 386.

Analysis for: $C_{22}H_{15}ClN_4O \cdot 1/5 H_2O$. Calculated: C, 67.68; H, 3.98; N, 14.35. Found: C, 67.87; H, 3.81; N, 14.00.

EXAMPLE 6

8-Benzoyl-3-Chloro-8,9,10,11-tetrahydro-7H-pyrido[3',4':4,5]pyrrolo[3,2-c]quinoline A mixture of 21.91 g (113 mmol) of 7-chloro-2-hydrazinoquinoline, 23 g (113 mmol) of N-benzoyl piperidone and 90 ml of ethanol are stirred at room temperature for 3 hours. The reaction is diluted with 250 ml of water, producing a yellow precipitate and allowed to stir overnight. The yellow solid is collected by filtration and dried to yield 39.5 g (92%) of intermediate hydrazone.

A mixture of 10.0 g (26.3 mmol) of the hydrazone and 20 ml of diethylene glycol are stirred at 220° C. for 2.5 hours. The reaction mixture is cooled and diluted with 400 ml of water producing a yellow precipitate which is dissolved in chloroform. The layers are separated and the organic layer is dried over $MgSO_4$, filtered and concentrated under vacuum to produce a crude product which is recrystallized from ether/chloroform to yield 4.0 g (42%) of the title compound as a yellow solid: m.p. 275° C.; m/e 362 (M+H).

Analysis for: $C_{21}H_{16}ClN_3O \cdot 1\ H_2O$. Calculated: C, 66.40; H, 4.78; N, 11.06. Found: C, 66.86; H, 4.57; N, 10.83.

EXAMPLE 7

3-Chloro-7,9,10,11-tetrahydro-N-phenyl-8H-pyrido-[3',4':4,5]pyrrolo[3,2-c]quinoline-8-carboxamide A mixture of 0.35 g (1.4 mmol) of 3-chloro-8,9,10,11-tetrahydro-7H-pyrido[3',4':4,5]pyrrolo[3,2-c]quinoline 0.185 (1.6 mmol) of phenylisocyanate and 10 ml of tetrahydrofuran is stirred at room temperature for 3 days. The reaction mixture is filtered and the solid collected is triturated in ether to yield 0.35 g (68%) of the title compound as an off white solid: m.p.>260° C.; m/e 299.

Analysis for: $C_{21}H_{27}ClN_4O$. Calculated: C, 66.93; H, 4.55; N, 14.87. Found: C, 67.01; H, 4.68; N, 14.87.

EXAMPLE 8

3-Chloro-8,9,10,11-tetrahydro-8-(4-pyridinylcarbonyl)-7H-pyrido[3',4':4,5]pyrrolo[3,2-c]quinoline To a mixture of 0.45 g (1.75 mmol) of 3-chloro-8,9,10,11-tetrahydro-7H-pyrido[3',4':4,5]pyrrolo[3,2-c]quinoline, 0.707 g (6.99 mmol) of triethylamine and 5 ml of dimethylformamide at ice-water bath temperature is added dropwise a solution of 0.247 g (1.75 mmol) of isonicotinoyl chloride hydrochloride and 1 ml of dimethylformamide. The reaction mixture is allowed to stir overnight while slowly reaching room temperature. A white precipitate is formed which is collected by filtration, washed with water and dried to yield 0.320 (50%) of the title compound as a white solid: m.p.>250° C.; m/e 362.

Analysis for: $C_{20}H_{15}ClN_4O \cdot \frac{1}{4} H_2O$. Calculated: C, 65.40; H, 4.25; N, 15.25. Found: C, 65,27; H, 4.24; N, 15.11.

EXAMPLE 9

3-Chloro-8-(2-furanylcarbonyl)-8,9,10,11-tetrahydro-7H-pyrido[3',4':4,5]pyrrolo[3,2-c]quinoline The same reaction procedure and workup is followed as for the compound of Example 8 using 0.50 g (1.94 mmol) of 3-chloro-8,9,10,11-tetrahydro-7H-pyrido[3',4':4,5]pyrrolo[3,2-c]quinoline and 0.253 g (1.94 mmol) of 2-furoylchloride to yield 0.12 g (17%) of the title compound as a white solid: m.p >250° C.; m/e 351.

Analysis for: $C_{19}H_{14}ClN_3O_2$. Calculated: C, 64.87; H, 4.01; N, 11.94. Found: C, 64.52; H, 3.40; N, 11.95.

EXAMPLE 10

8-(Benzo[b]thien-2-ylcarbonyl)-3-chloro-8,9,10,11-tetrahydro-7H-pyrido[3',4':4,5]pyrrolo[3,2-c]quinoline The same reaction procedure is followed as for the compound of Example 8, using 0.50 g (1.94 mmol) of 3-chloro-8,9,10,11-tetrahydro-7H-pyrido]3',4':4,5]pyrrolo[3,2-c]quinoline and 0.382 g (1.94 mmol) of thianaphthene-2-carbonylchloride. The reaction mixture is diluted with water and is stirred for 2 hours producing a brown precipitate which is collected by filtration. Purification by trituration with methanol/chloroform-/hexane followed by flash column chromatography (8% methanol in chloroform) yields 0.20 g (25%) of the title compound as a white solid: m.p.>250° C.; m/e 417.

Analysis for: $C_{23}H_{16}ClN_3OS$. Calculated: C, 66.10; H, 3.86; N, 10.05. Found: C, 65.93; H, 3.84; N, 10.05.

EXAMPLE 11

3-Chloro-8,9,10,11-tetrahydro-8-(2-thienylsulfonyl)-7H-pyrido [3',4':4,5]pyrrolo[3,2-c]quinoline The same reaction procedure is followed as for the compound of Example 8, using 0.50 g (1.94 mmol) of 3-chloro-8,9,10,11-tetrahydro-7H-pyrido [3',4':4,5]pyrrolo[3,2-c]quinoline and 0.354 g (1.94 mmol) of 2-thiophenesulfonyl chloride. The reaction solution is diluted with water and is stirred for 2 hours. The resulting precipitate is collected by filtration and triturated with methanol/chloroform/hexane to yield 0.575 g (78%) of the title compound as an off white solid: m.p.>250° C.; m/e 403.

Analysis for: $C_{18}H_{14}ClN_3O_2S_2 \cdot \frac{1}{2}H_2O$. Calculated: C, 52.36; H, 3.66; N, 10.18. Found: C, 52.04; H, 3.46; N, 10.09.

EXAMPLE 12

3-Chloro-7,9,10,11-tetrahydro-8H-pyrido[3',4':4,5]pyrrolo-[3,2-c]quinoline-8-carboxylic Acid Phenyl Ester A suspension of 0.30 g (1.16 mmol) of 3-chloro-8,9,10,11-tetrahydro-7H-pyrido[3',4':4,5]pyrrolo[3,2-c]quinoline in 8 ml of tetrahydrofuran is placed in an ice bath under nitrogen. Phenylchloroformate (0.182 g/1.16 mmol), dissolved in 1 ml of tetrahydrofuran is added dropwise and the reaction solution is allowed to stir overnight while slowly reaching room temperature. The reaction mixture is diluted with water and the precipitate is collected by filtration. The crude product is purified by flash column chromatography (4% methanol in chloroform) to yield 0.100 g of product contaminated with phenol. The product is then dissolved in chloroform and washed with 0.5N NaOH. The organic layer is then concentrated under vacuum to yield 0.080 g (18%) of the title compound: m.p.>250° C.; m/e 377.

Analysis for: $C_{21}H_{16}ClN_3O_2 \cdot \frac{3}{4}H_2O$. Calculated: C, 64.46; H, 4.50; N, 10.70. Found: C, 64.40; H, 4.25; N, 10.48.

Following the procedure of Example 7 and using an appropriate isocyanate or thioisocyanate, there are prepared the following ureas and thioureas.

EXAMPLE 13

N-Benzoyl-3-chloro-7,9,10,11-tetrahydro-8H-pyrido-[3',4':4,5]pyrrolo[3,2-c]quinoline-8-carboxamide 29% yield; m.p. 164°-166° C.; beige solid.

Analysis for: $C_{22}H_{17}ClN_4O_2 \cdot \frac{1}{4}H_2O$ Calculated: C, 64.55; H, 4.30; N, 13.69. Found: C, 64.63; H, 4.26; N, 13.69.

EXAMPLE 14

3-Chloro-7,9,10,11-tetrahydro-N-phenyl-8H-pyrido-[3',4':4,5]pyrrolo[3,2-c]quinoline-8-carbothioamide 71% yield; m.p. 231°-232° C.; off white solid.

Analysis for: $C_{21}H_{17}ClN_4S$. Calculated: C, 64.20; H, 4.36; N, 14.26. Found: C, 64.11; H, 4.33; N, 14.05.

EXAMPLE 15

4-[[(3-Chloro-7,9,10,11-tetrahydro-8H-pyrido[3',4':4,5-]pyrrolo-[3,2-c]quinoline-8-yl)carbonyl]amino]benzoic acid ethyl ester 65% yield; m.p. >250° C.; off-white solid.

Analysis for: $C_{24}H_{21}ClN_4O_3$. Calculated: C, 64.21; H, 4.72; N, 12.48. Found: C, 64.13; H, 4.67; N, 12.29.

EXAMPLE 16

3-Chloro-7,9,10,11-tetrahydro-N-(phenylmethyl)-8H-pyrido-[3',4':4,5]pyrrolo[3,2-c]quinoline-8-carboxamide 66% yield; m.p. >250° C.; beige solid.

Analysis for: $C_{22}H_{19}ClN_4O \cdot 1/5 H_2O$ Calculated: C, 66.99; H, 4.96; N, 14.20. Found: C, 66.62; H, 4.83; N, 13.81.

EXAMPLE 17

N-[(3-Chloro-7,9,10,11-tetrahydro-8H-pyrido[3',4':4,5]-pyrrolo[3,2-c]quinolin-8-yl)thioxo]benzamide 6% yield; m.p. 178°–180° C.; yellow solid.

Analysis for: $C_{22}H_{17}ClN_4OS$. Calculated: C, 62.78; H, 4.07; N, 13.31. Found: C, 62.90; H, 4.04; N, 13.43.

EXAMPLE 18

3-Chloro-7,9,10,11-tetrahydro-N-(phenylmethyl)-8H-pyrido-[3',4':4,5]pyrrolo[3,2-c]quinoline-8-carbothioamide 63% yield; m.p. 241°–242° C.; beige solid.

Analysis for: $C_{22}H_{19}ClN_4S$. Calculated: C, 64.93; H, 4.71; N, 13.77. Found: C, 64.82; H, 4.71; N, 13.78.

EXAMPLE 19

3-Chloro-7,9,10,11-tetrahydro-N-(phenylsulfonyl)-8H-pyrido-[3',4':4,5]pyrrolo[3,2-c]quinoline-8-carboxamide 8% yield; m.p. 199°–201° C.; yellow solid.

Analysis for: $C_{21}H_{17}ClN_4O_3S \cdot \frac{1}{2}H_2O$. Calculated: C, 56.06; H, 4.03; N, 12.45. Found: C, 55.96; H, 3.84; N, 12.50.

EXAMPLE 20

3-Chloro-7,9,10,11-tetrahydro-N-(3-methoxyphenyl)-8H-pyrido-[3',4':4,5]pyrrolo[3,2-c]quinoline-8-carboxamide 76% yield; m.p. >250° C.; white solid.

Analysis for: $C_{22}H_{19}ClN_4O_2$. Calculated: C, 64.94; H, 4.71; N, 13.77. Found: C, 64.70; H, 4.84; N, 13.91.

EXAMPLE 21

3-Chloro-8,9,10,11-tetrahydro-8-[(4-methoxyphenyl)-sulfonyl]-7H-pyrido[3',4':4,5]pyrrolo[3,2-c]quinoline Following the procedure of Example 11 and using 4-methoxyphenylsulfonyl chloride there is obtained the title compound, 50% yield; m.p. >250° C.; off-white solid.

Analysis for: $C_{21}H_{18}ClN_3O_3S$. Calculated: C, 58.94; H, 4.24; N, 9.82. Found: C, 58.83; H, 4.12; N, 9.84.

EXAMPLE 22

The ability of the compounds of the invention to inhibit interleukin 1 is measured by the ability of the test compounds to inhibit the IL-1-induced release of neutral protease from rabbit articular chondrocytes.

This assay is carried out as follows:

Isolation of rabbit chondrocytes:

Male New Zealand White rabbits are anesthetized with 50 mg/kg of ketamine (i.m.) and killed by an intracardiac injection of 3 mls. of Nembutal. The knee joints of both legs are resected and the articular surfaces are exposed. Cartilage slices are obtained using a scalpel and are placed in a tissue culture dish (100 mm diameter) containing 10 mls of Hank's balanced salt solution (HBSS). The chondrocytes within the cartilage slices are then liberated by a series of enzyme digestions. The slices are incubated for 10 minutes at 37° C. in 0.05% hyaluronidase (Sigma H-3884), rinsed with HBSS and incubated with 0.2% trypsin (Sigma T-2395) for 10 minutes at 37° C. The slices are rinsed again and incubated for 10 minutes at 37° C. with 1.2% collagenase (Sigma C-5138). The slices are then rinsed again with HBSS and resuspended in 10 ml of Ham's F-12 medium containing 10% fetal bovine calf serum (FCS) and 0.2% collagenase and incubated overnight at 37° C. in a 5% $CO_2$ incubator. The next day, the medium containing the digested cartilage fragments and liberated chondrocytes is transferred to a 15 ml centrifuge tube and the cells are collected by centrifugation and washed twice and resuspended in Ham's F-12 medium. The cells are then plated into 24-well tissue culture plates ($2 \times 10^5$ cells/well) and incubated at 37° C. until confluent (usually 4–6 days).

Stimulation of chondrocytes and drug treatment:

The confluent chondrocytes are rinsed twice with serum-free Ham's F-12 medium and 1 ml is added to each well. Fifty μl of purified human IL 1 (100 Units/ml; Genzyme Corporation, Boston, Mass.) is then added to stimulate these cells to secrete neutral protease. To measure drug effects, the cells are treated with test compound 10 minutes prior to addition of IL-1. The standard screening dose is 10 μM. Twenty-four hours after IL-1 stimulation, supernatant fluids are collected and assayed for neutral protease activity.

Neutral protease assay:

The neutral protease activity of chondrocyte supernatant fluids is determined by their ability to degrade an insoluble protease substrate, azocoll (Sigma). Supernatants are treated for 10 minutes at room temperature with 350 μM p-aminophenylmurcuric acetate to activate the latent enzyme. Three hundred μl of supernatant is then mixed with 500μl of a 20 mg/ml suspension of azocoll and incubated at 37° C. for 18–24 hours with gentle rocking. The mixtures are centrifuged and the amount of substrate hydrolyzed is determined by measuring the absorbance of the supernatant at 520 nm.

Drug effects are calculated as the % change in enzyme activity (absorbance) by supernatants from drug-treated chondrocytes relative to enzyme activity of supernatants from vehicle-treated chondrocytes as follows:

$$\% \text{ Inhibition of Protease Secretion} = \frac{A_{520} \text{ Untreated Supernatant} - A_{520} \text{ Drug Treated Supernatant}}{A_{520} \text{ Untreated Supernatant}} \times 100$$

When tested in this assay, the compounds of the invention gave the following results:

| Compound of Example No. | Dose (μM) | % Inhibition (I.S.D.) |
| --- | --- | --- |
| 1 | 10 | 40 |
| 2 | 10 | 38 |
| 3 | 10 | 22 |

-continued

| Compound of Example No. | Dose (μM) | % Inhibition (I.S.D.) |
|---|---|---|
| 4 | 10 | 64 (IC$_{50}$ = 7.3 μM) |
|   | 1 | 20 |
|   | 0.1 | 14 |
| 5 | 10 | 28 |
| 6 | 10 | 57 |
| 7 | 10 | 21 |
| 8 | 10 | 35 |
| 9 | 10 | 36 |
| 10 | 10 | 24 |
| 11 | 1 | <20 |
| 12 | 10 | <20 |

The results show that the compounds tested exhibit a moderate to very significant inhibition of IL-1 induced protease secretion.

EXAMPLE 23

The ability of the compounds of the invention to modify the process of bone resorption is evaluated in the bone resorption assay measuring $^{45}$Ca release from rat limb bones.

This assay is carried out as follows:

Limb bone preparation. Timed pregnant Sprague-Dawley CD® rats (Charles River) are administered 100 μCi $^{45}$CaCl$_2$ (NEN calcium -45 NEZ-013) in 100 μl of 0.9% saline, subcutaneously, on day 18 of gestation. The rats are sacrificed the following day by CO$_2$ asphyxiation. The fetuses are removed and the right forelimbs excised and placed in a Petri dish containing ice cold explant medium consisting of modified BGJ$_b$-Fitton Jackson media (custom formulation, Gibco No. 78-0088) adjusted to pH 7.3 to which 10 mM TES is added. The modified BGJ$_b$ media is obtained without salts, glucose or bicarbonate and is supplemented before use with 0.1 mM MgCl$_2$, 1.25 mM CaCl$_2$, 5.3 mM KCl, 0.7 mM MgSO$_4$, 130 mM NaCl, 1.0 mM NaH$_2$PO$_4$, 1 g/L glucose, 50 mg/L Na acetate and 100 U/ml penicillin G. The medium is sterilized by passage through a 0.2 μM filter (Nalge). Under a dissecting microscope, the bones are gently cleaned of adherent tissue and the cartilaginous ends removed. Incubation and drug treatment. The midshafts are placed, individually, on 3×3 mm squares of filter paper (Gelman GN-6 metricel filters; 0.45 μM pore size) which rest on stainless steel screens in wells of 24-well culture plates containing 0.5 mL of preincubation medium. The preincubation medium is brought to 37° C. prior to transfer of bones. The preincubation medium consists of the modified BGJ$_b$ medium (with salts and glucose as above), pH 7.3, containing 29 mM NaHCO$_3$. After incubation for 18-24 hours at 37° C. in 5% CO$_2$, the bones are transferred on their screen/filter paper supports to new plates containing, in a total volume of 0.5 mL/well at 37° C., the test compound diluted in preincubation medium supplemented with 15% heat inactivated horse serum (Gibco No. 230-6050), pH 7.3, with a bone resorption stimulating agent (e.g. parathyroid hormone [PTH] or interleukin-1 [IL-1]). For compounds that require nonaqueous solvents, dilutions are made from the appropriate stock solution with medium. In these instances, basal and bone resorption stimulated controls exposed to an equivalent concentration of the vehicle are included. An additional group of bones that have been subjected to boiling for 1 hour (kill control) are used to establish background, non cell mediated, exchange of $^{45}$Ca. The right ulna and radius from each fetus are used. Both bones are subjected to the same treatment and each treatment group consists of bones from 4 or more fetuses. Treatments are randomly assigned using a preclinical statistics program (PS-ALLOC). After a 48 hour incubation at 37° C. in 5% CO$_2$, the bones are removed from the medium and extracted in 0.5 mL of 0.1N HCl for 1 or more days. Duplicate 150 μL aliquots of the incubation medium and the bone extract are analyzed for $^{45}$Ca radioactivity in 5 mL of liquid scintillation cocktail.

The percentage of bone $^{45}$Ca released into the medium is determined as follows:

$$\frac{^{45}\text{Ca CPM in medium}}{^{45}\text{Ca CPM in medium} + ^{45}\text{Ca CPM in bone}} \times 100$$

Results are normally expressed as the ratio of the percent $^{45}$Ca release of the experimental group versus the appropriate vehicle control, or as an IC$_{50}$ value.

When tested in this assay, compounds of the invention give the following results:

| Compound of Example No. | Inhibition of Bone Resorption | |
|---|---|---|
|   | PTH-Induced | IL-1 Induced |
| 1 | Active, IC$_{50}$ = 0.633 μg/ml | Active, IC$_{50}$ = 6.84 μg/ml |
| 2 | Active, IC$_{50}$ = 0.98 μg/ml | Active, IC$_{50}$ = 3.39 μg/ml |
| 4 |   | Active at <5 μg/ml |
| 6 | Active at 10 μg/ml | Active at 5 μg/ml |
| 7 | Active at 10, 5 and 1 μg/ml | Active at 10 μg/ml |
| 8 | Active at 10 μg/ml | Active, IC$_{50}$ = 1.96 μg/ml |
| 9 | Active, IC$_{50}$ = 2.88 μg/ml | Active, IC$_{50}$ = 0.307 μg/ml |
| 10 |   | Active, IC$_{50}$ = 0.067 μg/ml |
| 11 | Active, IC$_{50}$ = 0.144 μg/ml | Active, IC$_{50}$ = 0.018 μg/ml |
| 12 | Active, IC$_{50}$ = 0.274 μg/ml | Active, IC$_{50}$ = 0.76 μg/ml |
| 13 | Active, IC$_{50}$ = 0.944 μg/ml | Active, IC$_{50}$ = 1.71 μg/ml |
| 14 | Active, IC$_{50}$ = 1.2 μg/ml | Active, IC$_{50}$ = 1.21 μg/ml |
| 15 | Active, IC$_{50}$ = 5.5 μg/ml |   |
| 16 | Active, IC$_{50}$ = 2.52 μg/ml | Active, IC$_{50}$ = 6.22 μg/ml |
| 17 | Active, IC$_{50}$ = 1.16 μg/ml | Active, IC$_{50}$ = 1.65 μg/ml |
| 18 |   | Active, IC$_{50}$ = 2.39 μg/ml |
| 20 | Active, IC$_{50}$ = 0.059 μg/ml | Active, IC$_{50}$ = 0.0088 μg/ml |
| 21 |   | Active, IC$_{50}$ = 8.48 μg/ml |

What is claimed is:

1. A compound having the formula

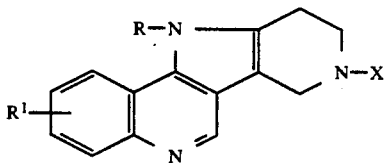

wherein

R is hydrogen, lower alkyl or phenyl;

R¹ is hydrogen, lower alkyl, phenyl, halo, hydroxy, lower alkoxy or trifluoromethyl;

R² is phenyl, phenylloweralkyl, thienyl, furyl, pyrrolyl, pyridyl, benzothienyl, benzofuryl, indolyl, quinolinyl, or any of the foregoing substituted with halo, lower alkyl, lower alkylcarbonyl, benzoyl, carboxy, lower alkoxycarbonyl, $OR^3$, $N(R^3)_2$, $CON(R^3)_2$, phenylsulfonyl, lower alkylsulfonyl, cyano, nitro or trifluoromethyl;

R³ is hydrogen, lower alkyl or phenyl;

X is R², $-CO_2R^2$, $-CO_2R^4$, $-\overset{Y}{\underset{\|}{C}}NHR^2$, $-\overset{Y}{\underset{\|}{C}}NHR^4$, $-SO_2R^2$, $-SO_2R^4$, $-\overset{Y}{\underset{\|}{C}}NHSO_2R^2$ or $-\overset{Y}{\underset{\|}{C}}NHSO_2R^4$;

R⁴ is lower alkyl;

Y is —O— or —S—.

2. The compound of claim 1, having the name 3-chloro-8,9,10,11-tetrahydro-8-[4-(methylsulfonyl)phenyl]-7H-pyrido[3',4':4,5]pyrrolo[3,2-c]quinoline.

3. The compound of claim 1, having the name 4-(3-chloro-8,9,10,11-tetrahydro-7H[3',4':4,5]pyrrolo[3,2-c]quinolin-8-yl)benzoic acid ethyl ester.

4. The compound of claim 1, having the name 4-(3-chloro-8,9,10,11-tetrahydro-7H-pyrido[3',4':4,5]pyrrolo[3,2-c]quinolin-8-yl)benzonitrile.

5. The compound of claim 1, having the name 3-chloro-7,9,10,11-tetrahydro-N-phenyl-8H-pyrido[3',4':4,5]pyrrolo[3,2-c]quinoline-8-carboxamide.

6. The compound of claim 1, having the name 3-chloro-7,9,10,11-tetrahydro-8H-pyrido[3',4':4,5]pyrrolo[3,2-c]quinoline-8-carboxylic acid phenyl ester.

7. The compound of claim 1, having the name N-benzoyl-3-chloro-7,9,10,11-tetrahydro-8H-pyrido[3',4':4,5]pyrrolo[3,2-c]quinoline-8-carboxamide.

8. The compound of claim 1, having the name 3-chloro-7,9,10,11-tetrahydro-N-phenyl-8H-pyrido[3',4':4,5]pyrrolo[3,2-c]quinoline-8-carbothioamide.

9. The compound of claim 1, having the name 4-[[(3-chloro-7,9,10,11-tetrahydro-8H-pyrido[3,'4':4,5]pyrrolo[3,2-c]quinoline-8-yl)carbonyl]amino]benzoic acid ethyl ester.

10. The compound of claim 1, having the name 3-chloro-7,9,10,11-tetrahydro-N-(phenylmethyl)-8H-pyrido-[3',4': 4,5]pyrrolo[3,2-c]quinoline-8-carboxamide.

11. The compound of claim 1, having the name N-[(3-chloro-7,9,10,11-tetrahydro-8H-pyrido[3',4':4,5]pyrrolo[3,2-c]quinolin-8-yl)thioxo]benzamide.

12. The compound of claim 1, having the name 3-chloro-7,9,10,11-tetrahydro-N-(phenylmethyl)-8H-pyrido-[3', 4':4,5]pyrrolo[3,2-c]quinoline-8-carbothioamide.

13. The compound of claim 1, having the name 3-chloro-7,9,10,11-tetrahydro-N-(phenylsulfonyl)-8H-pyrido[3',4': 4,5]pyrrolo[3,2-c]quinoline-8-carboxamide.

14. The compound of claim 1, having the name 3-chloro-7,9,10,11-tetrahydro-N-(3-methoxyphenyl)-8H-pyrido[3',4':4,5]pyrrolo[3,2-c]quinoline-8-carboxamide.

15. The compound of claim 1, wherein the compound administered is 3-chloro-8,9,10,11-tetrahydro-8-(2-thienylsulfonyl)-7H-pyrido[3',4':4,5]pyrrolo[3,2-c]-quinoline.

16. The compound of claim 1, wherein the compound administered is 3-chloro-8,9,10,11-tetrahydro-8-[(4-methoxyphenyl)sulfonyl]-7H-pyrido[3',4':4,5]-pyrrolo[3,2-c]quinoline.

17. A method for the treatment of inflammatory conditions which comprises the administration of a therapeutic amount of a compound having the formula

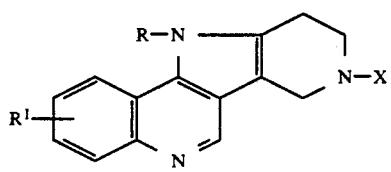

wherein

R is hydrogen, lower alkyl or phenyl;

R¹ is hydrogen, lower alkyl, phenyl, halo, hydroxy, lower alkoxy or trifluoromethyl;

R² is phenyl, benzoyl, phenylloweralkyl, phenylsulfonyl, thienyl, furyl, pyrrolyl, pyridyl, benzothienyl, benzofuryl, indolyl, quinolinyl, or any of the foregoing substituted with halo, lower alkyl, lower alkylcarbonyl, benzoyl, carboxy, lower alkoxycarbonyl, $OR^3$, $N(R^3)_2$, $CON(R^3)_2$, phenylsulfonyl, lower alkylsulfonyl, cyano or trifluoromethyl;

R³ is hydrogen, lower alkyl or phenyl;

X is $-\overset{}{\underset{\|}{C}}R^2$ and $-\overset{}{\underset{\|}{C}}R^3$; and
     Y                    Y Y is —O— or —S—.

18. The method of claim 17, wherein the compound administered is 3-chloro-8,9,10,11-tetrahydro-8-(2-thienylcarbonyl)-7H-pyrido[3',4':4,5]pyrrolo[3,2-c]-quinoline.

19. The method of claim 17, wherein the compound administered is 3-chloro-8-(4-cyanobenzoyl)-8,9,10,11-tetrahydro-7H-pyrido[3',4':4,5]pyrrolo[3,2-c]-quinoline.

20. The method of claim 17, wherein the compound administered is 8-benzoyl-3-chloro-8,9,10,11-tetrahydro-7H-pyrido[3',4':4,5]pyrrolo[3,2-c]quinoline.

21. The method of claim 17, wherein the compound administered is 3-chloro-8,9,10,11-tetrahydro-8-(4-pyridinylcarbonyl)-7H-pyrido[3',4':4,5]pyrrolo[3,2-c]quinoline.

22. The method of claim 17, wherein the compound administered is 3-chloro-8-(2-furanylcarbonyl)-8,9,10,11-tetrahydro-7H-pyrido[3',4':4,5]pyrrolo[3,2-c]-quinoline.

23. The method of claim 17, wherein the compound administered is 8-(benzo[b]thien-2-ylcarbonyl)-3-chloro-8,9,10,11-tetrahydro-7H-pyrido[3',4':4,5]-pyrrolo[3,2-c]quinoline.

* * * * *